United States Patent
Pain et al.

(10) Patent No.: US 8,403,944 B2
(45) Date of Patent: Mar. 26, 2013

(54) APPARATUS FOR PLACING STITCH TURNS RESULTING FROM A SHAPE-MEMORY METAL THREAD

(75) Inventors: Bernard Pain, Monistrol sur Loire (FR); Olivier Cuilleron, Saint Priest en Jarez (FR)

(73) Assignee: Microval, Saint Just Malmont (FR)

( * ) Notice: Subject to any disclaimer, the term of this patent is extended or adjusted under 35 U.S.C. 154(b) by 91 days.

(21) Appl. No.: 12/746,691

(22) PCT Filed: Dec. 12, 2008

(86) PCT No.: PCT/FR2008/052287
§ 371 (c)(1),
(2), (4) Date: Jul. 21, 2010

(87) PCT Pub. No.: WO2009/081004
PCT Pub. Date: Jul. 2, 2009

(65) Prior Publication Data
US 2010/0305582 A1    Dec. 2, 2010

(30) Foreign Application Priority Data
Dec. 13, 2007 (FR) .................................... 07 59801

(51) Int. Cl.
*A61B 17/10* (2006.01)
(52) U.S. Cl. ........................................ 606/139; 606/151
(58) Field of Classification Search .......... 606/139–151, 606/213, 215–217; 227/176.1, 177.1, 175.1–182.1
See application file for complete search history.

(56) References Cited

U.S. PATENT DOCUMENTS

| | | | |
|---|---|---|---|
| 4,223,674 A * | 9/1980 | Fluent et al. | 604/507 |
| 4,400,170 A * | 8/1983 | McNaughton et al. | 604/62 |
| 4,531,938 A * | 7/1985 | Kaye et al. | 604/62 |
| 6,132,438 A * | 10/2000 | Fleischman et al. | 606/139 |
| 6,457,625 B1 * | 10/2002 | Tormala et al. | 227/177.1 |
| 6,592,508 B1 * | 7/2003 | Ravins et al. | 600/8 |
| 6,699,255 B1 | 3/2004 | Cushchieri et al. | |
| 6,837,893 B2 * | 1/2005 | Miller | 606/139 |

(Continued)

FOREIGN PATENT DOCUMENTS

| | | |
|---|---|---|
| WO | 0007506 A | 2/2000 |
| WO | 2007017562 A | 2/2007 |

OTHER PUBLICATIONS http://www.thefreedictionary.com/axis, definition of the term axis retrieved on May 7, 2012.*
International Search Report for PCT/FR2008/052287 dated Jun. 9, 2009.

*Primary Examiner* — Ryan Severson
*Assistant Examiner* — David Eastwood
(74) *Attorney, Agent, or Firm* — Heslin Rothenberg Farley & Mesiti P.C.

(57) ABSTRACT

The device comes in the form of a gun with a body, a grip handle and a control component. The body has coaxially a hollow protruding aiming rod equipped, at its free end, with a cylinder containing the threads. The rod is capable, under the action of the control component, of allowing a thread ejection needle to move so that a loop is formed on emergence from the cylinder. The cylinder is mounted at the end of a fixed translation axis and engaged inside the rod; the other end of said axis engaging with a mechanism capable of partially rotating it and the cylinder, when said control component is released, in order to position another thread opposite said ejection needle.

8 Claims, 6 Drawing Sheets

U.S. PATENT DOCUMENTS

| | | | |
|---|---|---|---|
| 2002/0082615 A1* | 6/2002 | Shipp et al. | 606/139 |
| 2003/0105473 A1* | 6/2003 | Miller | 606/139 |
| 2003/0105475 A1* | 6/2003 | Sancoff et al. | 606/139 |
| 2004/0087979 A1* | 5/2004 | Field et al. | 606/148 |
| 2004/0153101 A1* | 8/2004 | Bolduc et al. | 606/143 |
| 2005/0033318 A1* | 2/2005 | Miller et al. | 606/139 |
| 2005/0070922 A1* | 3/2005 | Field et al. | 606/139 |
| 2008/0045978 A1* | 2/2008 | Kuhns et al. | 606/142 |

* cited by examiner

APPARATUS FOR PLACING STITCH TURNS RESULTING FROM A SHAPE-MEMORY METAL THREAD

CROSS REFERENCE TO RELATED APPLICATIONS

This application is a national stage filing under section 371 of International Application No. PCT/FR2008/052287 filed on Dec. 12, 2008, and published in French on Aug. 20, 2009 as WO 2009/081004 and claims priority of French application No. 0759801 filed on Dec. 13, 2007, the entire disclosure of these applications being hereby incorporated herein by reference.

BACKGROUND ART

The invention relates to the technical field of devices for securing and immobilizing a meshed structure acting as a prosthesis on an anatomical part.

These meshed structures acting as prostheses, are very well known and can, for example, be used for the inguinal area since they are intended for the laparoscopic or open repair of inguinal hernias. This type of implant may be immobilized by different means, such as suture wires, clips, etc.

The invention relates more specifically to a way of securing and immobilizing a meshed structure acting as a prosthesis using an element made from a preformed thread capable of:
  constituting at least one loop in the idle state, in other words when not being acted upon in any way;
  being expanded linearly after insertion in a tubular element;
  resuming its original shape upon emerging from the tube.

To advantage but non-restrictively, the threads are made out of a shape-memory material. Such a solution is clear from the teaching in the document WO 2007/017562 whereof the applicant of the present application is also the proprietor.

From this basic conception, the meshed structure immobilization element, the problem arises of fitting said element which, in the idle state, is constituted by a loop, so that, prior to being fitted, it has to be expanded linearly, and then resume its original shape, constituting at least one loop implemented in a part of the thickness of the anatomical part and through a plurality of meshes of the structure in order to provide the connections.

To attain this objective, the document WO 2007/017562 teaches that a plurality of threads should be arranged, in alignment in a tube which has means capable of extracting a thread at the moment of its impaction in the meshed structure. This solution is not however completely satisfactory, given that a certain difficulty has arisen in respect of fitting a plurality of loops in the expanded state inside the tube with risks of overlapping, in particular at the moment of fitting.

The intended purpose of the invention is to overcome these drawbacks in a straightforward, safe, effective and rational way.

The problem the invention sets out to resolve is the possibility of fitting a meshed structure immobilisation element, said element constituting, in the idle state, i.e. when it is not being acted upon in any way, at least one loop, with the objective of being able to fill a fitting device with a plurality of threads in the linearly expanded state and extracting each thread separately from the device, while constituting at least one loop implemented in a part of the thickness of the anatomical part through a plurality of meshes of the structure in order to provide a connection.

BRIEF SUMMARY OF INVENTION

To resolve said problem, a device has been designed and perfected for putting in suture loops made from a shape-memory metal thread, the device comes in the form of a gun with a body, a grip handle and a control component, said body having coaxially a hollow protruding aiming rod.

According to the invention, the rod is fitted, at its free end, with a cylinder containing the threads, said rod being subject to means capable, under the action of the control component, of allowing a thread ejection means to move so that a loop is formed on emergence from the cylinder and then, when said control component is released, of partially rotating said cylinder in order to position another thread opposite said ejection means.

Given these characteristics, it only remains to apply a pressing stress, with the rod fitted with the cylinder, on the fastening zones under consideration and to act upon the control component in order to eject a thread and concomitantly form a loop through the meshes of the structure and of the corresponding anatomical part.

To resolve the problem posed by controlling the cylinder, the cylinder is mounted at the end of a translationally fixed axial shaft and engaged inside the rod, the other end of the shaft engaging with means capable of partially rotating the shaft and, consequently, the cylinder.

To resolve the problem posed by rotating the cylinder as a loop is being fitted, the means capable of partially rotating the shaft and the cylinder are constituted by a rotating toothed ring angularly indexed on the shaft and whereof the teeth have one profiled end engaged in a complementary profile of a set of teeth formed at the end of a bushing securely mounted in the body. On said bushing, is mounted, with capacity for guided linear movement and indexation in rotation, a sleeve inside which the toothed ring is mounted against a spring, said sleeve being movable coaxially under the action of the control component.

To resolve the problem posed by ejecting the metal thread, the sleeve is mounted with capacity for coaxial movement against a return spring and is interdependent with a tube mounted to slide on the shaft, the tube being subject to the ejection means for the purpose of moving it into alignment with a housing of the cylinder.

To resolve the problem posed by coupling the cylinder, the ejection means is a needle coupled at one of its ends with a guide interdependent with the sliding tube and guided, at its other end, in a nozzle interdependent with the rod.

In one embodiment, the end of the shaft has a flat bearing surface engaging with a complementary internal coaxial bearing surface of the cylinder.

According to another feature, the cylinder is mounted in a sheath, coupled, in a removable way, with the nozzle, said sheath accommodating a protective and supporting element that has a through orifice communicating with the housing of the cylinder placed opposite the ejection needle.

The control component is a trigger articulated on the body whereof one end has a fork engaging with a boss of the sleeve.

BRIEF DESCRIPTION OF DRAWING FIGURES

The invention is disclosed hereinafter in further detail by means of the figures of the appended drawings wherein.

DETAILED DESCRIPTION

Figure 1:
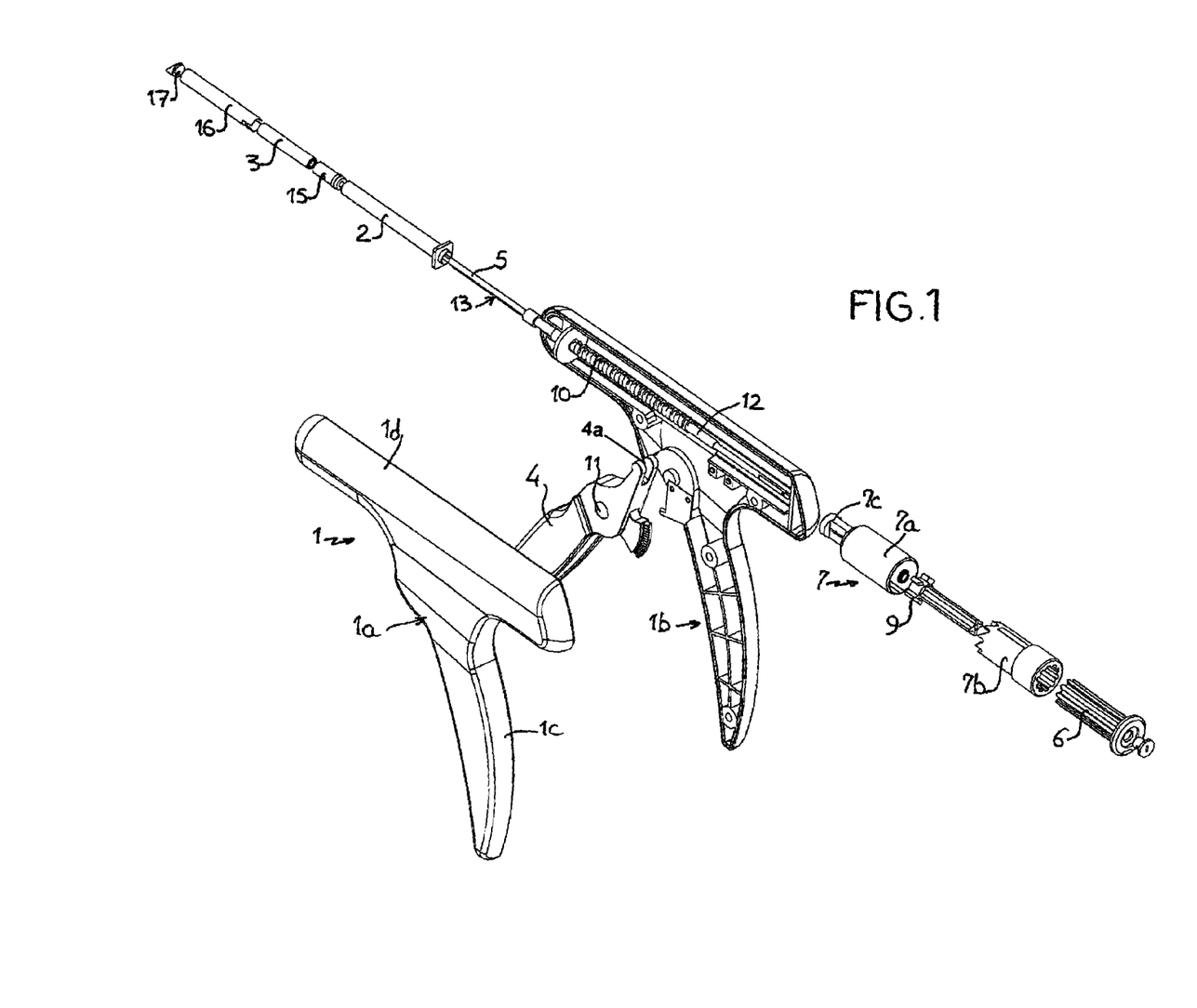
FIG. 1 is a perspective view of the main elements of the device prior to assembly.
Figure 2:
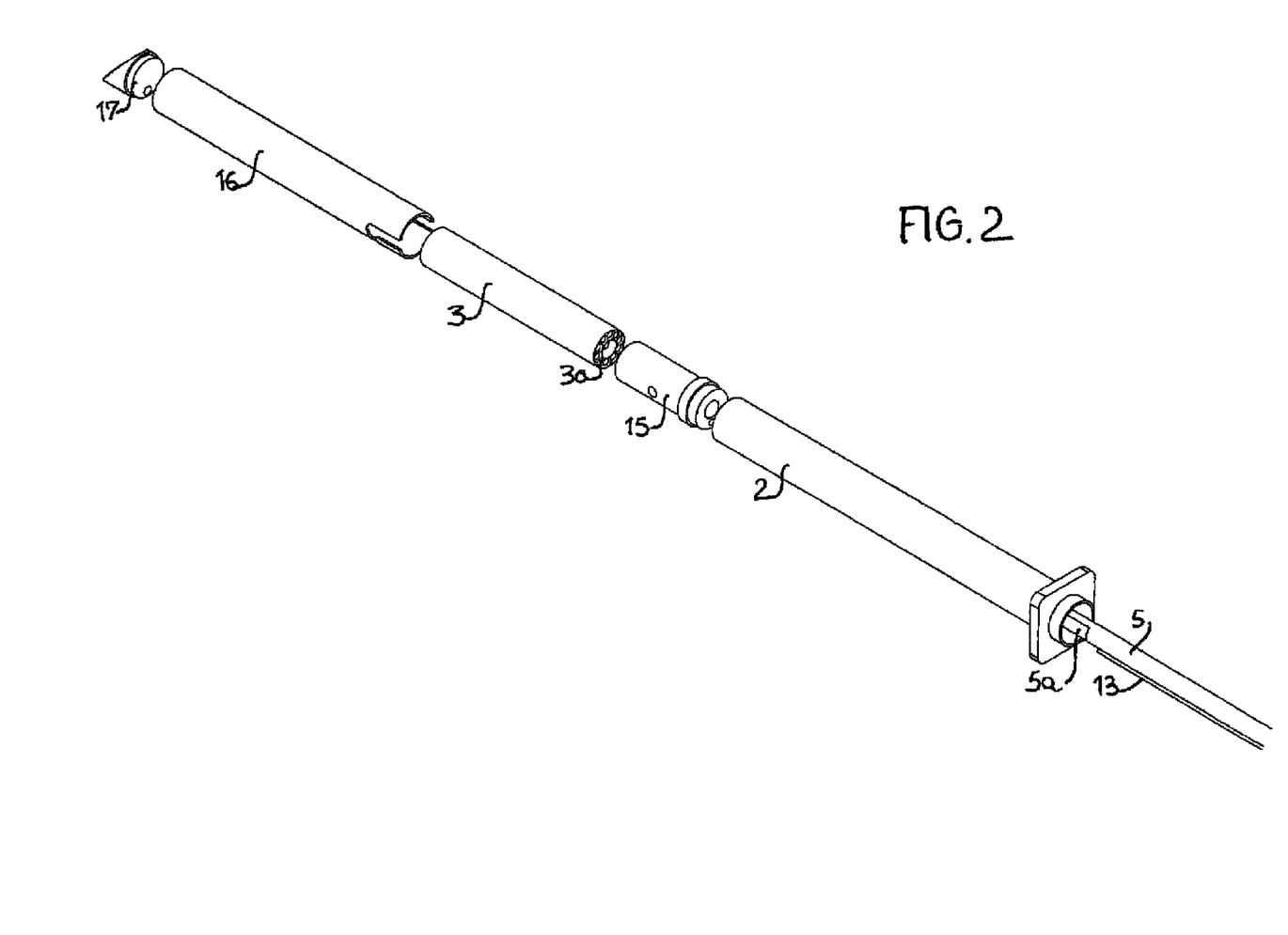
FIG. 2 is a larger-scale perspective view showing the assembly of the elements relative to the coupling of the cylinder.
Figure 3:
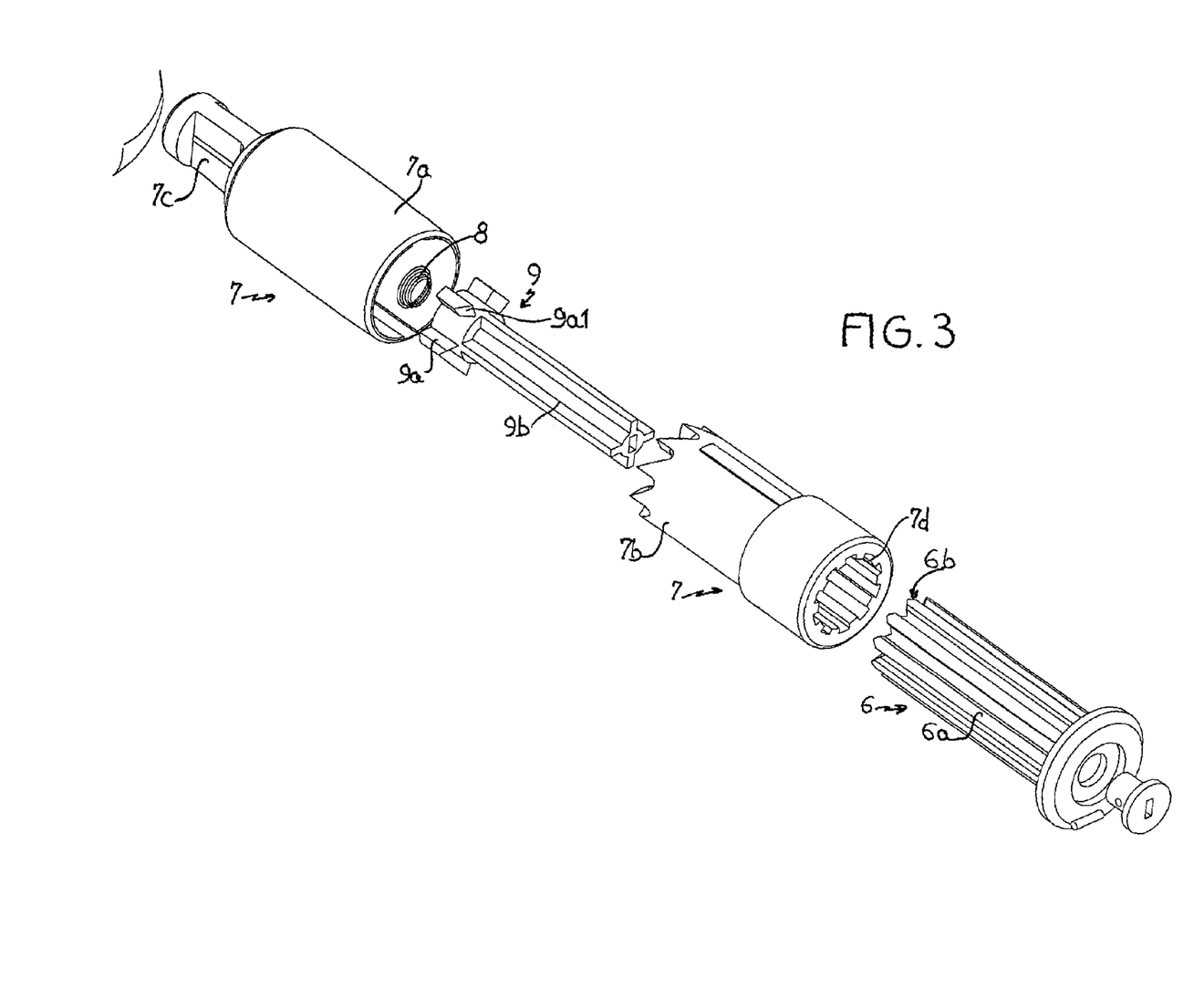
FIG. 3 is a perspective view, on a larger-scale prior to assembly, of the main elements showing an embodiment of the cylinder rotation means.
Figure 4:
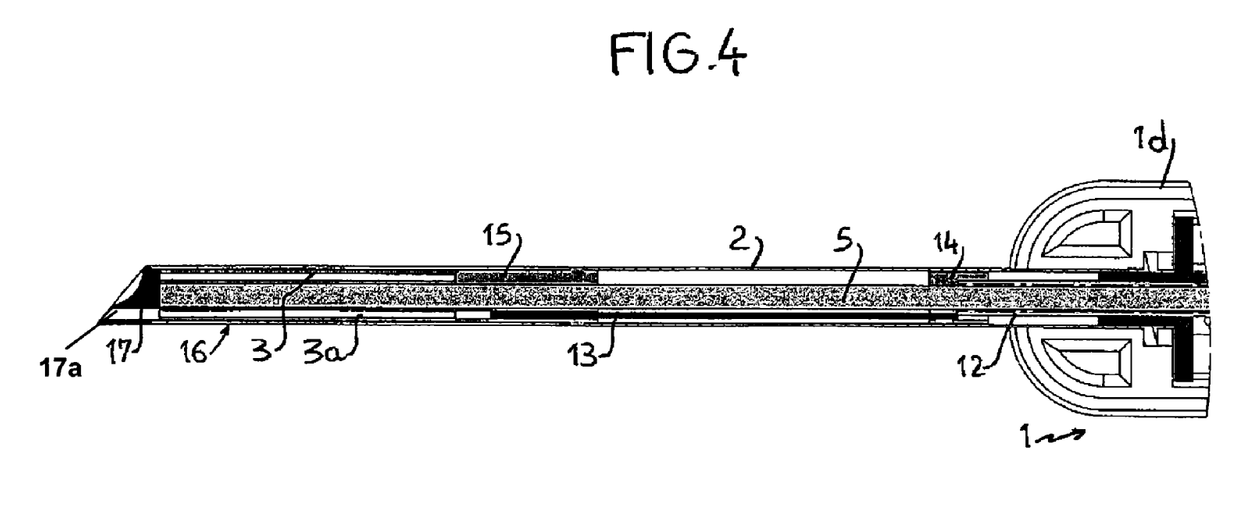
FIG. 4 is a longitudinal cross-section view of the end of the rod.
Figure 5:
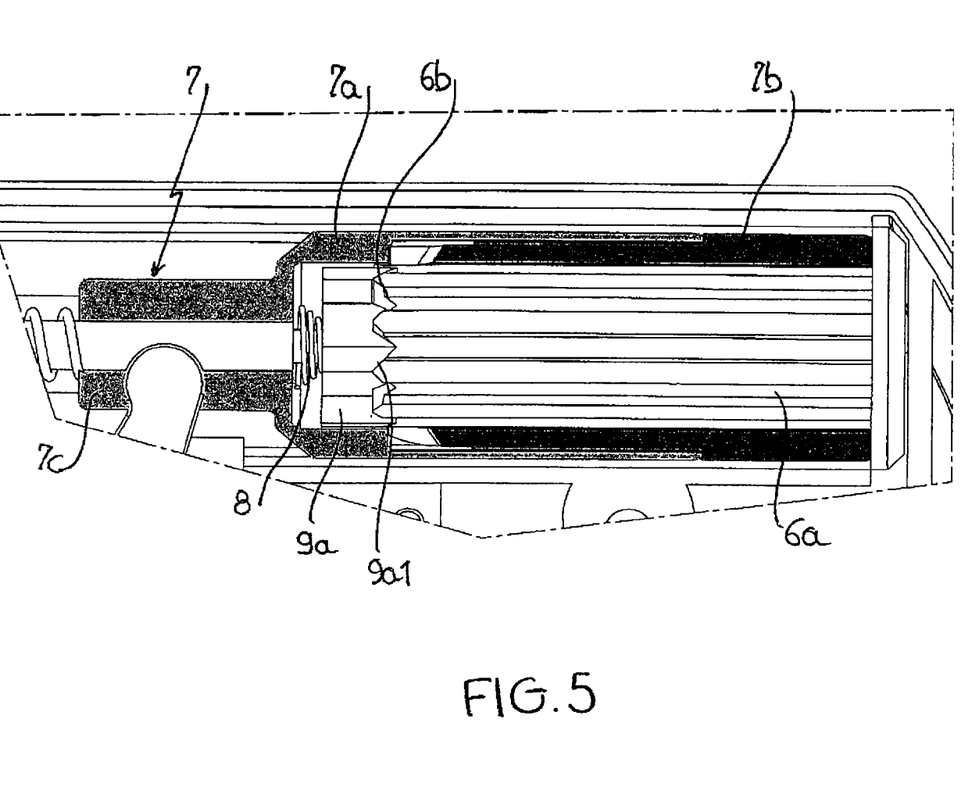
FIG. 5 is a longitudinal cross-section view of the cylinder rotation arrangements.
Figure 6:
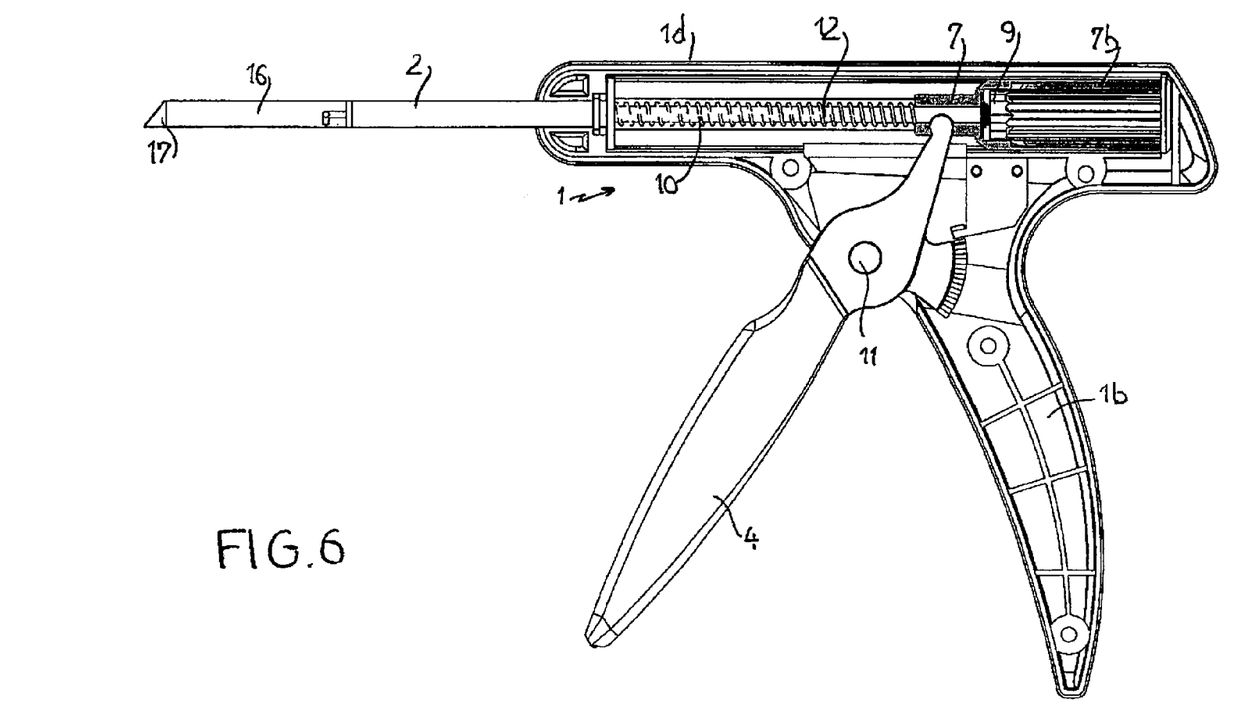
FIG. 6 is a partial longitudinal cross-section view of the entire device after the elements are assembled.

It will be remembered, as is clear from the teaching in the document WO 2007/017562 that the element for immobilizing the prosthetic meshed structure is made from a thread modelled so as to constitute, in the idle state, at least one loop. The thread is made out of a material selected to be expanded linearly, after insertion into a component of tubular cross-section, and to resume its loop shape when it emerges from said component. To advantage, the thread may be made out of a shape-memory material.

According to the invention, the device, for fitting this type of loop, comes in the general shape of a gun. The gun has a body (1) made, for example, from two half-shells of plastic material (1a) and (1b) forming a grip handle (1c) established angularly from a barrel (1d) of general tubular shape. The barrel (1d) is interdependent with an aiming rod (2) at the end of which is mounted, according to an underlying inventive feature, a cylinder (3). The housings (3a) of the cylinder (3) are each intended to accommodate a thread in order to form a loop in the conditions previously indicated.

As will be indicated in the remainder of the description, the rod (2) is subject to means capable, under the action of a control component (4), of allowing a thread ejection means to move so that a loop is formed on emergence from the cylinder (3), and then, at each pulse given on the control component (4), of partially rotating said cylinder (3) in order to position another of its housings (3a) containing a thread, opposite said ejection means.

In the embodiment shown in the figure drawings, the cylinder (3) is secured, with capacity for disassembly, at one end of a translationally fixed axial shaft (5) mounted inside the body (1d) and engaged in the rod (2). For example, the end of the shaft (5) has a flat bearing surface (5a) engaging with a coaxial bearing surface, of complementary cross-section, presented by the cylinder (3). The other end (5b) of the shaft is a slave to means capable of partially rotating the shaft and, concomitantly, the cylinder (3). The other end of the shaft (5) is coupled with a bushing (6) securely mounted inside the body (1), and in particular at the end of the part (1d) acting as the barrel, on the opposite side from the one accommodating the rod (2).

The bushing (6) accommodates, with capacity for guided linear movement and indexation in rotation, a sleeve (7). For example, the bushing (6) may have peripherally a series of splines (6a) engaging with complementary splines (7d) formed in the bore of the sleeve (7). Inside the sleeve (7), is mounted in rotation, against a spring (8), a toothed ring (9). For example, the ring (9) has a head (9a) with, peripherally, a set of teeth (9a1). This head is extended by a bearing surface (9b) freely engaged in the bore of the bushing (6). The ends of the teeth (9a1) of the ring (9) have a profile acting as a ramp, engaging with a complementary profile (6b) of a set of teeth formed at the end of the bushing (6).

The sleeve (7) can be moved coaxially under the action of the control component (4), against a return spring (10). In the example shown, the sleeve (7) is made in two parts (7a) and (7b), joined together, to constitute a unitary assembly. Quite clearly, a single piece casting design (7) for the sleeve is conceivable. The control component (4), substantially in the form of a trigger, is articulated on a transverse axis (11) and has a fork (4a) engaging, for example, with a discontinuity (7c) of the sleeve (7) in order to drive it in translatory motion, under a swivelling effect relative to the axis (11).

The sleeve (7), for example the part (7a), is interdependent with a tube (12) mounted to slide on the shaft (5) inside the rod (2). This tube (12) is subject to the ejection means for the purpose of moving it into alignment with a housing (3a) of the cylinder (3), after rotation thereof. In the embodiment shown, the ejection means is constituted by a needle (13) coupled at one of its ends with a guide (14) interdependent with the sliding tube (12). At its other end, the needle (13) is freely engaged in a nozzle (15), interdependent with the rod (2). This nozzle (15) also acts as a bearing for the shaft (5) controlling the rotation of the cylinder (3).

In the embodiment shown, the cylinder (3) is mounted inside a sheath (16) coupled, in a removable way, with the nozzle (15). For example, the sheath (16) is fitted on a cylindrical bearing surface of the nozzle (15). At the free end of the sheath (16), is mounted a protective and supporting element (17) that has a through orifice (17a), communicating with the housing under consideration (3a) of the cylinder (3) placed opposite the ejection needle (13).

The sheath (16), accommodating the cylinder (3), may have means for the visual inspection of the load status of said cylinder.

The operation of the device is particularly straightforward and effective, and it is easy to use for practitioners.

The cylinder (3) is previously filled, in each compartment (3a), with a thread constituting, in the idle state, the suture loop. For information purposes, the cylinder may come with ten housings. When so filled, the cylinder (3) is coupled at the end of the shaft (5) stopped against the nozzle (15). After the sheath (16) is fitted onto the nozzle (15), in alignment with the rod (2) and the protective element (17), the device is ready for use.

The practitioner places the aiming rod (2) equipped, as shown, with the cylinder (3) the sheath (16) and the element (17), so that it presses on the part of the meshed structure which is to be secured to a corresponding part of the anatomy, by means of the loop. In this position, the result of pressing the trigger (4) is to control the translatory motion of the sheath (7) equipped with the tube (12) and, consequently, to move the ejection needle (13) which will push the thread placed in the corresponding housing of the cylinder. The thread pushed by the needle (13), emerges through the orifice (17a) of the protective element (17) to allow its impaction through the meshes of the prosthetic plate and into the thickness of the corresponding anatomical part. As shown, under the effect of the release of the thread, at least one loop is formed that immobilizes and secures the corresponding part of the meshed structure.

Importantly, under the effect of the aforementioned movement, the toothed ring (9), through its tooth profile escapes from the complementary profile (6b) and, under the thrust effect of the spring (8), falls back into an adjacent tooth profile causing, concomitantly, like a pawl, the rotation of said ring and, consequently, of the shaft (5) accommodating at the end the cylinder (3). The ensuing result is a partial rotation of the cylinder (3) so that another housing can be brought into line opposite the ejection needle (13). The device is consequently ready for another suture loop to be put in place.

The ring (9), particularly through the bearing surface (9b), is indexed angularly on the shaft (5), so that the partial rotation of this ring brings about the partial rotation of the shaft (5).

Given these features, it is possible to use, with the same device, a plurality of cylinders that are ready and filled with suture wires.

In a preferred way, the device is intended to be disposed of after each use.

Likewise, without thereby departing from the context of the invention, the device can be used to fit and secure any type of suture implant of general elongated, and in particular filiform, shape.

The advantages are clear from the description, and in particular the following are stressed and must be remembered:
  the use of a preformed loop
  the use of a rotary cylinder that allows a plurality of loops to be fitted, with no need to reload;
  the ease-of-use of the device, given that it is merely necessary to press and release the trigger;
  the simplicity of implementation;
  the operational reliability.

The invention claimed is:

1. A device for putting in suture loops made from a shape-memory metal thread, the device having a form of a gun with a body having a barrel, a grip handle and a control component, a hollow aiming rod extending coaxially beyond a first end of the barrel, a cylinder containing said shape-memory metal threads, extending coaxially beyond a free end of the aiming rod, said rod being subject to means, under action of the control component, for allowing a shape-memory metal thread ejection means to move so that a loop is formed on emergence of a shape-memory metal thread from the cylinder, wherein the cylinder is mounted to an end of a translationally fixed shaft extending inside and through the aiming rod into the barrel, an other end of said shaft engaging with means for partially rotating the shaft and, concomitantly, said cylinder, upon and by release of said control component, in order to position another shape-memory metal thread opposite said ejection means.

2. The device as claimed in claim 1, wherein the means for partially rotating the shaft and, concomitantly, the cylinder is located in the barrel near an end of the barrel opposite the first end, and comprises: a rotating toothed ring angularly indexed on the shaft, teeth of the toothed ring having a profiled end engaged in a complementary profile of a set of teeth formed at an end of a bushing securely mounted in the body, on said bushing, is mounted, for guided linear movement and indexation in rotation, a sleeve inside which is mounted the toothed ring against a spring, said sleeve being movable coaxially under the action of the control component.

3. The device as claimed in claim 2, wherein the sleeve is mounted for coaxial movement against a return spring.

4. The device as claimed in claim 2, wherein the sleeve is interdependent with a tube mounted to slide on the shaft, said tube being subject to the shape-memory metal thread ejection means for the purpose of moving the tube into alignment with a housing of the cylinder.

5. The device as claimed in claim 4, wherein the shape-memory metal thread ejection means comprises a needle coupled at one end of the needle with a guide interdependent with the sliding tube and guided, at an other end of the needle, in a nozzle interdependent with the aiming rod.

6. The device as claimed in claim 1, wherein the end of the shaft has a flat bearing surface engaging with a complementary internal coaxial bearing surface of the cylinder.

7. The device as claimed in claim 5, wherein the cylinder is mounted in a sheath coupled, in a removable way, with the nozzle, said sheath accommodating a protective and supporting element that has a through orifice communicating with a housing of the cylinder placed opposite the needle.

8. The device as claimed in claim 2, wherein the control component is a trigger articulated on the body whereof one end has a fork engaging with a boss of the sleeve.

* * * * *